(12) United States Patent
Gifford et al.

(10) Patent No.: US 8,858,718 B2
(45) Date of Patent: Oct. 14, 2014

(54) PLATE WASHING SYSTEM WITH ULTRASONIC CLEANING OF PIPES AND A CONTROL METHOD THEREOF

(75) Inventors: Robert M. Gifford, Starksboro, VT (US); Lenore Buehrer, Burlington, VT (US); Thomas A. Cleveland, Colchester, VT (US)

(73) Assignee: BTI Holdings, Inc., Winooski, VT (US)

( * ) Notice: Subject to any disclaimer, the term of this patent is extended or adjusted under 35 U.S.C. 154(b) by 865 days.

(21) Appl. No.: 12/243,822

(22) Filed: Oct. 1, 2008

(65) Prior Publication Data

US 2009/0032064 A1 Feb. 5, 2009

Related U.S. Application Data

(63) Continuation-in-part of application No. 11/183,867, filed on Jul. 19, 2005, now abandoned, which is a continuation-in-part of application No. 10/939,467, filed on Sep. 14, 2004, now abandoned.

(51) Int. Cl.
| | | |
|---|---|---|
| B08B 7/00 | (2006.01) |
| B08B 7/04 | (2006.01) |
| B01L 99/00 | (2010.01) |
| B08B 3/12 | (2006.01) |
| B08B 3/04 | (2006.01) |
| G01N 35/10 | (2006.01) |
| B08B 9/00 | (2006.01) |
| G01N 35/00 | (2006.01) |

(52) U.S. Cl.
CPC ........... *B08B 3/044* (2013.01); *B08B 2209/005* (2013.01); *B01L 99/00* (2013.01); *B01L 2200/143* (2013.01); *B08B 3/12* (2013.01); *B01L 2300/0864* (2013.01); *B01L 2400/0487* (2013.01); *G01N 35/1004* (2013.01); *B01L 2400/0439* (2013.01); *B01L 2300/0829* (2013.01); *B08B 9/00* (2013.01); *G01N 2035/00554* (2013.01)

USPC ............ 134/18; 134/1; 134/22.1; 134/22.18; 134/42; 134/184; 422/510; 422/517

(58) Field of Classification Search
USPC ........ 134/1, 18, 22.1, 22.11, 42, 184; 422/99, 422/100, 501, 502, 504, 510, 517
See application file for complete search history.

(56) References Cited

U.S. PATENT DOCUMENTS 3,213,670 A * 10/1965 MacGeorge ................... 73/37.6
5,380,487 A 1/1995 Choperena et al.
(Continued)

FOREIGN PATENT DOCUMENTS

| JP | 01254871 | 10/1989 |
| JP | 09 021730 A | 1/1997 |

(Continued)

OTHER PUBLICATIONS

Attachment 3 to Declaration by Briar Alpert—Bio-Tek Instruments Automated Microplate Washer Model EL402 Operator's Manual, Manual Part No. 4020080, Revision C, Sep. 1987.

(Continued)

*Primary Examiner* — Alexander Markoff
(74) *Attorney, Agent, or Firm* — Sughrue Mion, PLLC

(57) ABSTRACT

An automated method of cleaning the pipes of a plate washing system is provided. The plate washing system includes at least one manifold having a plurality of pipes configured to be provided within wells of a plate in order to wash the wells, an ultrasonic transducer mounted to a tank, and a control system. The plate washing system also includes sensors to sense the position of the pipes relative to plate and the tank, and the fluid level within the wells of the plate. The method includes dispensing fluid to the tank, submerging the tips of the pipes within the fluid, activating the ultrasonic transducer in order to vibrate the fluid, and aspirating the fluid from the tank. The control system may initiate a cleaning operation at the request of the user, at a scheduled interval, or when the level sensing system detects a decrease in instrument function.

61 Claims, 8 Drawing Sheets

(56) References Cited

U.S. PATENT DOCUMENTS

| | | | |
|---|---|---|---|
| 5,951,783 | A | 9/1999 | Kontorovich et al. |
| 6,212,949 | B1 | 4/2001 | Inder et al. |
| 6,337,959 | B1 * | 1/2002 | Kwak et al. ............ 399/57 |
| 6,631,639 | B1 * | 10/2003 | Dam et al. ............ 73/290 V |
| 6,767,748 | B2 | 7/2004 | Yokokawa et al. |
| 6,835,352 | B2 | 12/2004 | Ito et al. |
| 2003/0198575 | A1 | 10/2003 | Noda et al. |
| 2004/0231438 | A1 | 11/2004 | Schwartz |

FOREIGN PATENT DOCUMENTS

| | | |
|---|---|---|
| JP | 11 304779 A | 11/1999 |
| JP | 2001 170538 A | 6/2001 |

OTHER PUBLICATIONS

Images 1-22 of Bio-Tek Instruments, Inc. video shown to Examiner Alexander Markoff on Mar. 13, 2007.

Declaration Under 37 C.F.R. § 1.132 signed and dated by Briar Alpert on Dec. 6, 2007 and all attachments therein.

Tecan, "Instructions for Use for COLUMBUS Washer" Manual, vol. 2.2, Mar. 2003. Particular relevance: p. 4-7; p. 4-12: point 4.5.5; p. 7-2: point 7.1.1. Original file name: D1_Instructions for use for COLUMBUS_Washer_V2_2.pdf. Attached as: Published-Evidence-1.pdf.

Tecan, "Service Contract COLUMBUS" Administration, Oct. 2008. Particular relevance: Entire document. Original file name: D10_ Service Contract Columbus.pdf. Attached as: Published-Evidence-10.pdf.

Tecan, "Gebrauchsanweisung fur den COLUMBUS Washer" Manual, May 2003. Particular relevance: p. 7-4; p. 4-12: point 4.5.5; p. 7-2: point 7.1.1. Original file name: D11_Gebrauchsanweisung fur den Columbus Washer, Mai 2003.pdf. Attached as: Published-Evidence-11.pdf.

Seehawer, C., "Grundlagen der Ultraschallreinigungstechnik" Presentation, Mar. 2002. Particular relevance: pp. 2-8, 13, and 24. Original file name: D3_Grundlagen_Ultraschallreinigungstechnik, Seehawer.pdf. Attached as: Published-Evidence-3.pdf.

Tecan, "Operating Manual TE-SONIC" Manual, vol. 1.0, May 2001. Particular relevance: p. 1-7, 1st paragr.; p. 1-9, 1st paragr. Original file name: D4_Operating Manual_TE-SONIC.pdf. Attached as: Published-Evidence-4.pdg.

Tecan, "Delivery Note/Invoice COLUMBUS Plate Washer" Administration, Mar. 2003. Particular relevance: Entire Document. Original File name: D6_Delivery Note_Invoice for Columbus_Jun. 2003. pdf. Attached as: Published-Evidence-6.pdf.

Multi channel Systems GmbH, "Protocol "Oocyte Preparation"" Protocol, Mar. 2004. Particular relevance: pp. 1 and 5. Original file name: D7_Protocol Oocyte Preparation, Multi channel Systems.pdf. Attached as: Published-Evidence-7.pdf.

Dr. Ing. Wulf. F., "Bericht der Fruhjahrstagung der Studiengruppe fur elektronische Instrumentierung vom 4.-6. Marz 2002, Darmstadt" Berlin: Dr. Ing. F. Wulf, 2002. ISBN: 1438-496. Particular relevance: pp. 70-87. Original file name: D8_Bericht der Fruhjahrstagung SEI_Marz 2002, ISSN 1438496.pdf. Attached as: Published-Evidence-8.pdf.

Tecan, "TE-SONIC—a powerful new detection device from TECAN for blood pooling and sample transfer verification." Press Release, Sep. 19, 2001. Particular relevance: Entire document. Original file name: D9_Press Release TE-SONIC, Sep. 2001.pdf. Attached as: Published-evidence-8.pdf.

Opposition Against European Patent EP 1 637 887, filed by OK Pat AG, Dr. Theodor Muller, European Patent Attorney, pp. 1-36, dated Apr. 15, 2010.

EPO Form 2300E; Notice of Opposition to a European Patent; evidence supporting opposition against European Patent EP 1 637 887, pp. 1-6, Apr. 15, 2010.

European Search Report of corresponding European Patent Application No. 09159456.4 dated Jun. 23, 2009.

* cited by examiner

PLATE WASHING SYSTEM WITH ULTRASONIC CLEANING OF PIPES AND A CONTROL METHOD THEREOF

CROSS-REFERENCE TO RELATED APPLICATIONS

This application is a Continuation-In-Part application of U.S. application Ser. No. 11/183,867, filed on Jul. 19, 2005, which is a Continuation-In-Part application of U.S. application Ser. No. 10/939,467, filed on Sep. 14, 2004. The entire disclosures of U.S. application Ser. Nos. 11/183,867 and 10/939,467 are incorporated herein by reference.

BACKGROUND OF THE INVENTION

1. Technical Field

This invention generally relates to a plate washing system with ultrasonic cleaning of pipes and a control method thereof. The ultrasonic cleaning system can provide cleaning of the plate washing system's dispense and aspirate pipes, and monitor the performance in terms of volumetric accuracy and precision.

2. Discussion of Related Art

Certain laboratory operations, such as immuno assays, require the testing of small samples which are carried out in an arrangement of microwells having volumes of, for example 50-300 microliters or less formed in microtiter plates, hereinafter referred to generically as well plates. An example of this type of laboratory operation is an Enzyme Linked ImmunoSorbent Assay ("ELISA") reaction which is performed for measuring the presence or absence of an antigen/antibody complex formed within the wells of the well plate.

Reactions of this type involve the addition and removal of liquid reagents within each well. Intentionally, some of the components in the reagent chemically bond to the well. Therefore, at several stages of the reactions, the unbound liquid and components remaining in the wells must be removed and the insides of the wells must be washed by dispensing a wash solution such as water, a buffer solution, or other fluid in the wells using and gravity feed or a pump, and then evacuating the liquid under a vacuum.

The wells can be arranged in a strip or in-line format, or can be arranged in a matrix format. Until recently, commonly used matrices were configured to have 8×12 wells spaced at 9 mm apart between centers, hereinafter referred to as a 96-well plate. However, with the advent of High Throughput Screening ("HTS"), two more matrixes were introduced which increased the total number of wells while keeping the overall size of the well plate the same: 1) the 384-well plate, as shown in FIG. 1, configured to 16×24 wells spaced at 4.5 mm apart between centers, and 2) the 1536-well plate configured to have 32×48 wells spaced at 2.25 mm apart between centers (not shown). Since the overall foot print of the these new well plates are the same as the 96-well plate, the size of the wells in the new micro titer well plates is necessarily smaller than those in the 96-well plates while the depth of the wells remains generally the same. However, this is not always the case.

A conventional washer used for removing the unbound contents in wells of a well plate includes dispense pipes for dispensing the wash solution into the wells of the plate (e.g., by a pump or gravity feed), and aspirate pipes for evacuation the solution from the wells of the well plate (e.g., by a vacuum or a suction device). In order to quickly wash the well plates, the washing process is performed simultaneously on as many wells of the well plate as possible. A commercial example of such a microplate washer is the Texan PW384.

As discussed in U.S. Pat. No. 5,951,783 issued to Kontorovich et al., which is herein incorporated by reference, the dispense and aspirate pipes can be provided on a single manifold assembly or separate dispense and aspirate manifolds.

In order to accommodate the well plates having smaller wells, the dispense and aspirate pipes must have small diameters. However, as a result of evaporation, the dispensed materials leave solid materials (such as salts from the assay reagents) within the pipes. The solid material residue can impact the performance of the pipes or even render the pipes inoperable. Impact on performance issues is currently not detectable within the microplate washing system and requires external instrumentation to detect volumetric dispense and aspiration errors.

Ultrasonic cleaning techniques have been used to remove the residual material from the aspirate and dispense pipes and return the pipes to an operative condition. These ultrasonic cleaning techniques use a commercially available ultrasonic tank of suitable size to allow immersion of the impaired pipe assemblies.

Although the use of ultrasonic cleaning is effective, ultrasonic cleaning using a commercially available tank is a complex process. It requires the addition of cleaning liquid in order to fill the tank, removal of the pipe assemblies from the microtiter plate washing system before the pipe assembly is inserted into the tank, removal of the waste material from the tank once the cleaning process has been completed, installation of the pipe assemblies on the plate washing system, and purging cleaning fluid from the pipe assemblies by dispensing.

SUMMARY OF THE INVENTION

It is therefore desirable to provide a plate washing system having an ultrasonic system, one or more sensors to verify that fluid was dispensed to or aspirated from the plate washing system, one or more sensors to confirm that the pipes have been moved to a position within the fluid of the ultrasonic cleaning tank, and a controller that initiates the ultrasonic cleaning process when one of the following conditions is met: the user instructs, via a command to the instrument controller, that the process of cleaning the pipes should commence; the user defines a time interval, frequency, or otherwise defined schedule, and the instrument controller commences the process of cleaning the pipes based on the user defined schedule; or the instrument controller uses one or more sensors to monitor the liquid level in the wells during a plate washing operation and commences the process of cleaning the pipes if the liquid level in one or more of the wells deviates from the user requested volume by a defined amount.

According to one aspect of the invention, a plate washing system includes at least one manifold having a plurality of pipes configured to be provided with wells of a plate in order to wash the wells; a tank that is capable of being filled with a fluid; an ultrasonic transducer mounted to the tank; and a control system. When the pipes are positioned within the tank, the control system activates the ultrasonic transducer in order to vibrate the fluid within the tank.

According to another aspect of the invention, a method of cleaning pipes of a plate washing system includes providing the washing system, including at least one manifold having a plurality of pipes configured to be provided within wells of a plate in order to wash the wells, a tank, an ultrasonic transducer mounted to the tank, and a control system; moving at least one of the manifolds and the tank so that tips of the plurality of pipes are positioned within the tank; filling the tank with a fluid; and activating the ultrasonic transducer in order to vibrate the fluid within the tank. The control system activates the ultrasonic transducer.

According to another aspect of the invention, a method of verification where a system can detect levels of fluid in the microplate wells to verify volumetric function via single or multiple level sensing probes is provided.

According to another aspect of the invention, a plate washing system includes at least one manifold having a plurality of pipes configured to be provided with wells of a plate in order to wash the wells; a tank that is capable of being filled with a fluid; an ultrasonic transducer mounted to the tank; and a control system that activates the ultrasonic transducer in order to vibrate the fluid within the tank. The control system automatically activates the ultrasonic transducer when the volumetric function of the pipes has been impaired.

BRIEF DESCRIPTION OF THE DRAWINGS

The advantages, nature and various additional features of the invention will appear more fully upon consideration of the illustrative embodiment of the invention which is schematically set forth in the drawings, in which.

DETAILED DESCRIPTION OF EXEMPLARY EMBODIMENTS OF THE INVENTION

Figure 1:
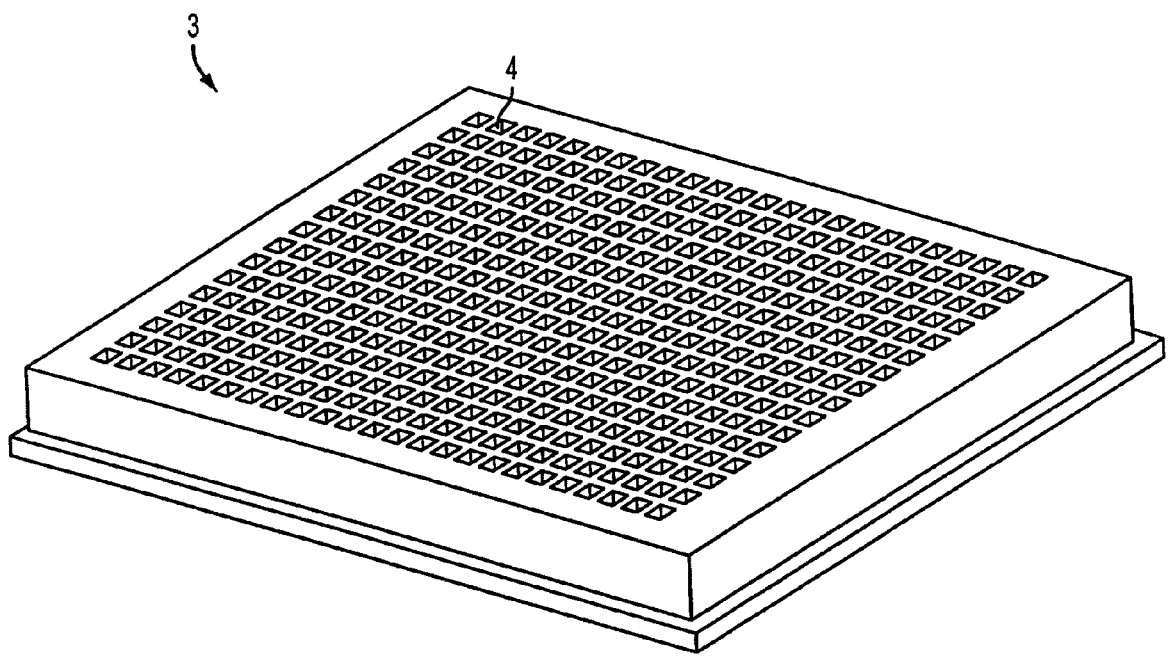
FIG. 1 is a perspective view of a conventional titer plate having 384 wells arranged in a 16×24 matrix.

While the invention is open to various modifications and alternative forms, specific embodiments thereof are shown by way of examples in the drawings and are described herein in detail. There is no intent to limit the invention to the particular forms disclosed.

Figure 2:
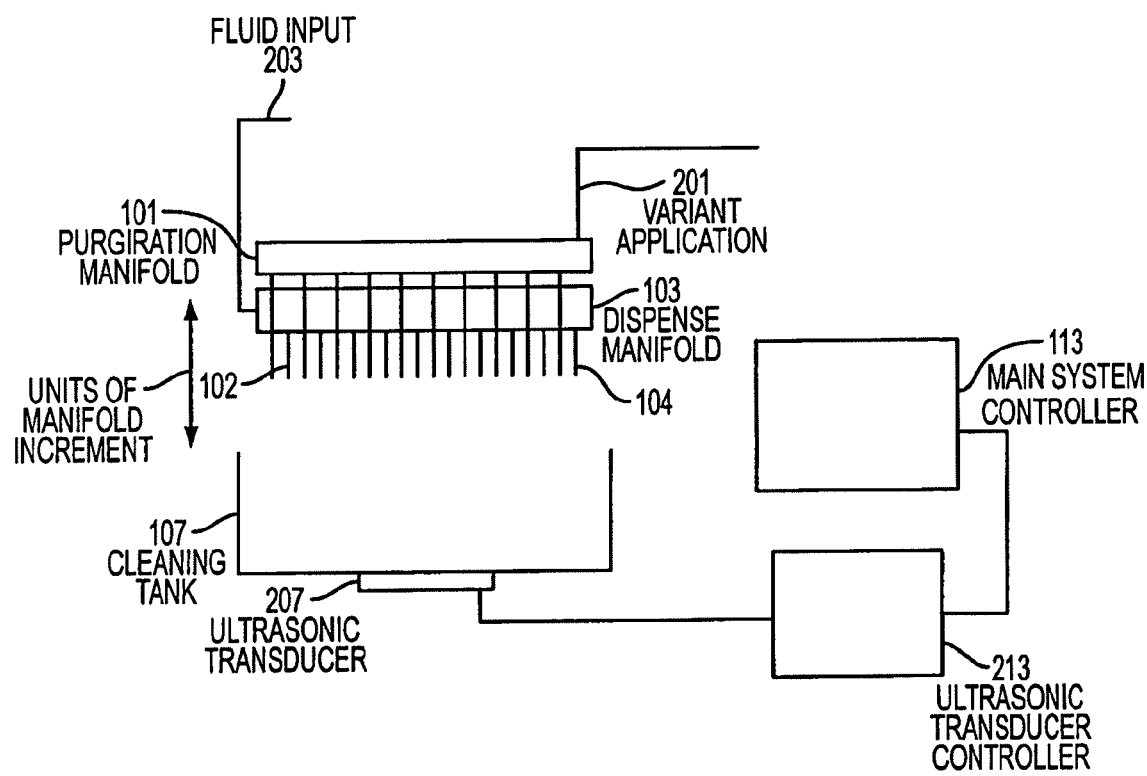
FIG. 2 is a schematic drawing of an embodiment of the system for cleaning a well plate washing system's dispense and aspirate pipes by using ultrasonic vibrations.

FIG. 2 generally shows a first non-limiting embodiment of an ultrasonic cleaning system of a plate washing system. The ultrasonic cleaning system includes a dispense manifold 103 having dispense pipes 102, an aspiration manifold 101 having aspirate pipes 104, a fluid input line 203, a vacuum aspiration line 201, a cleaning tank 107, and an ultrasonic transducer 207 mounted on the tank 107. However, the invention is not limited to separate dispense and aspiration manifolds and a single manifold containing both aspirate and dispense pipes can also be used.

In order to clean the pipes, the dispense and aspiration manifolds 103, 101 are lowered so that the pipes 102, 104 are within the cleaning tank 107. However, the invention is not limited in this respect. For example, instead the tank 107 could be raised to the level of the pipes 102, 104.

Then, a fluid is introduced into the cleaning tank 107 by the dispense pipes 102 in order to fill the tank 107 with fluid. This fluid can be, for example, a mild detergent or de-ionized water, as is discussed in detail below. However, the invention is not limited by the type of fluid.

The aspiration manifold 103 either draws the fluid from the tank 107 into the aspirate pipes 104 or vents the aspirate pipes 102 to atmospheric pressure. Either way, the aspirate pipes 104 can be filled with the fluid in the tank.

Once the tank 107 and pipes 102, 104 are filled with fluid, the ultrasonic transducer 207 is activated, or energized, causing the fluid in the tank 107 to vibrate. Since the tips of the pipes 102, 104 are submerged in the fluid, the vibration allows the fluid to fill and clean the dispense and aspirate pipes 102, 104. Once the cleaning has taken place, the aspirate pipes 104 are used to evacuate the cleaning tank 107.

A control system, including a main system controller 113 and ultrasonic transducer controller 213, automatically controls the movement of the pipes 102, 104, the dispensing of the fluid into the tank 107, the activation of the ultrasonic transducer 207, and the evacuation of the tank 107. However, the invention is not limited in this respect and additional controllers or a single controller could also be used.

Figure 3:
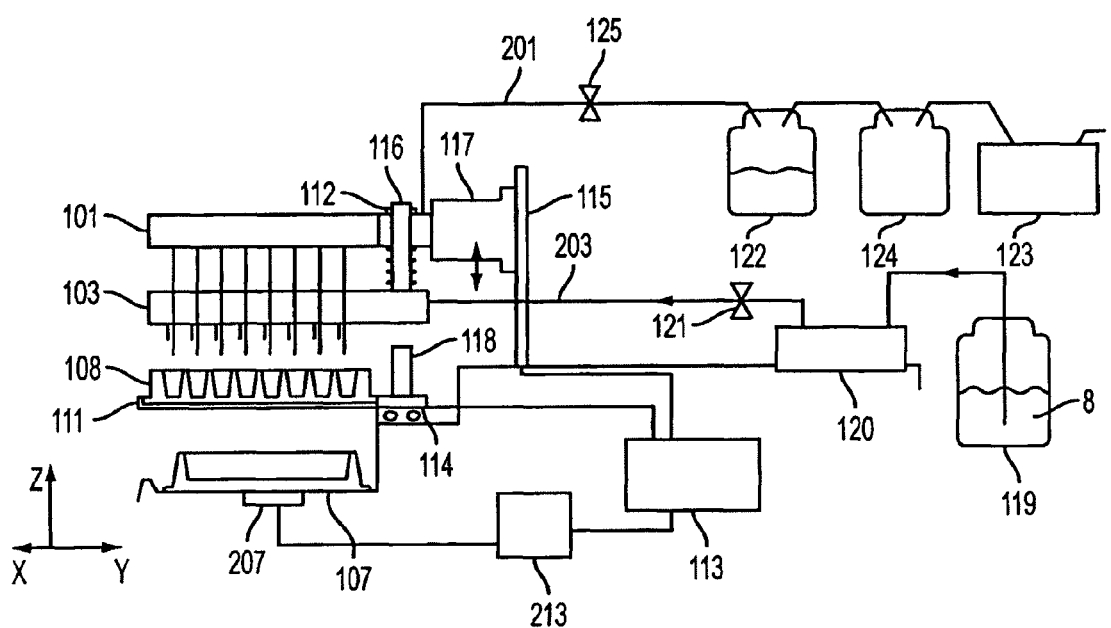
FIG. 3 is a schematic of a first embodiment of the well plate washing system.

Thus far, the discussion has been directed to the ultrasonic cleaning of the dispensing and aspiration pipes. FIG. 3 shows additional features of a non-limiting embodiment of the overall system for washing a microtiter well plate. In addition, a non-limiting method of cleaning a microtiter well plate, will be described below with respect to the microtiter plate washing system shown in FIG. 3.

A microtiter well plate 108 is positioned on a well plate support mechanism or carrier 111 which in turn is moved into a washing position by the support mechanism positioning system 114 connected to the main system controller 113. However, the invention is not limited by the type of support 111. The support mechanism positioning system is also used to index the support plate in the horizontal X-Y plane relative to the manifolds during a washing operation as required. Alternatively, a drive mechanism for moving the top manifold 101 and bottom manifold 103 in the X-Y plane can be used to achieve the desired relative motion during a wash operation.

In accordance with this embodiment, the bottom manifold 103 is the dispense manifold, which is slaved to the top aspirate manifold 101. However, the invention is not limited in this respect. The aspirate manifold 101 is lowered and raised along the linear guide way 115 along the z-axis by a driving mechanism 117 connected to the main system controller 113. The dispense manifold 103 is suspended from the aspirate manifold 101 by a linear guide 116 and stopped from descending beyond a predetermined position relative to top manifold by a first stop 112. Furthermore, a second stop 118 is provided on the support mechanism 111 for preventing the dispense manifold 103 from entering into the small wells during a wash operation as the aspirate manifold 101 is lowered to evacuate the wells. In order to clean the wells, a wash solution 8 is delivered into the dispense manifold from a source container 119 by means of a pump 120 and a valve 121 through the fluid input line 203. The wash solution 8 is removed from the aspirate manifold 101 through the vacuum aspiration line 201 into a waste container 122 which is separated from a vacuum pump 123 by a trap t24. An opening valve 125 connects the aspirate manifold 101 to the waste container.

When it is desired to clean the aspirate and dispense pipes 102, 104, the support mechanism 111 and second stop 118 are moved out of the way and placed in a home position. The main system controller 113 then lowers the top manifold 101 and bottom manifold 103, allowing their respective pipes to be lowered into the cleaning tank 107. Once the pipes 102, 104 are in position, the dispense pipes 102 provide a fluid to the tank 107, and the pipes 102, 104 are cleaned by the ultrasonic vibrations of the fluid within the tank 107, as is discussed in detail above with respect to FIG. 2.

In the pictured embodiment, the ultrasonic transducer 207 is mounted to the cleaning tank 107 with adhesive. However, the invention is not limited in this respect. For example, the transducer 201 can be mechanically attached to the cleaning tank 107 with a threaded attachment.

The ultrasonic transducer 207 includes a ceramic material that changes dimensions due to the piezoelectric effect when a voltage is applied to the ceramic material. When an alternating voltage at a frequency is applied to the ceramic material, the ceramic material vibrates at that frequency. If the transducer 207 is bonded to the tank 107 filled with liquid, the tank 107 also vibrates and the energy of vibration of the tank 107 can cause small bubbles to form and collapse throughout the liquid. The action of the bubbles collapsing (i.e., cavitation) provides cleaning of the tips of the pipes 102, 104 within the fluid.

In accordance with the first embodiment of the present invention, the main system controller 113 and ultrasonic transducer controller 213 automatically control the cleaning of the ultrasonic transducer 207 in accordance with a pre-programmed cleaning cycle. That is, the controllers 113, 213 can control the times when the pipes 104, 102 are cleaned and can control the duration of soaking of the pipes 104, 102.

For example, the ultrasonic transducer controller 213 or main system controller 113 controls the processes of filling the tank 107, lowing the manifolds 101, 103 (or single manifold), turning on the ultrasonic transducer 207, and evacuating the tank 107. In addition, the controllers 113, 213 can control whether this cleaning cycle is repeated and can control when the cleaning cycles occur.

Furthermore, the controllers 113, 213 can control fluid changes. For example, according to a preferred embodiment of the invention, the pipes 102, 104 are cleaned with a mild detergent and then rinsed with de-ionized water (DiH2O). First, the pipes are cleaned with the detergent, which reduces the surface tension in the water. This reduced surface tension increases cavitation and, as such, provides more cleaning action. Then, the pipes are rinsed with DiH2O.

According to the first embodiment, a single source container 119 is used for the well wash solution, detergent, and DiH2O. Therefore, whenever a change of the fluid within the source is required, the controllers 113, 213 cause a notification to be provided an operator.

Figure 4:
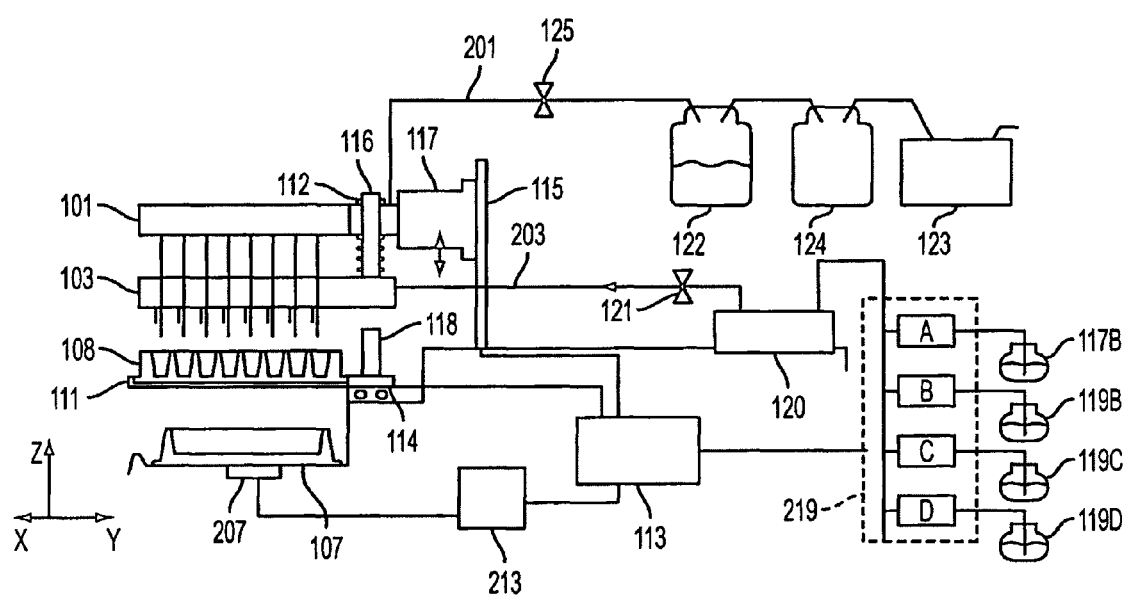
FIG. 4 is a schematic of a second embodiment of the well plate washing system in which multiple cleaning solutions are used.

Alternatively, according to a second non-limiting embodiment shown in FIG. 4, an external valve box 219 can be used. This valve box includes valves A-D, which are connected to multiple source containers 219A-D. If multiple source containers are used, then the controllers 113, 213 also control the dispensation of the appropriate fluid (e.g., well wash solution, detergent, or DiH2O).

In addition, the ultrasonic transducer controller 213 can control the voltage and frequency of the applied ultrasonic voltage. It is preferred that the applied voltage is 30 to 300V with a frequency of 40-100 kHz. For example, according to one design, the ultrasonic controller 213 uses 48 VDC and creates an ultrasonic signal at the transducer of ±300V at 50 kHZ. However, the invention is not limited in this respect.

Figure 5:
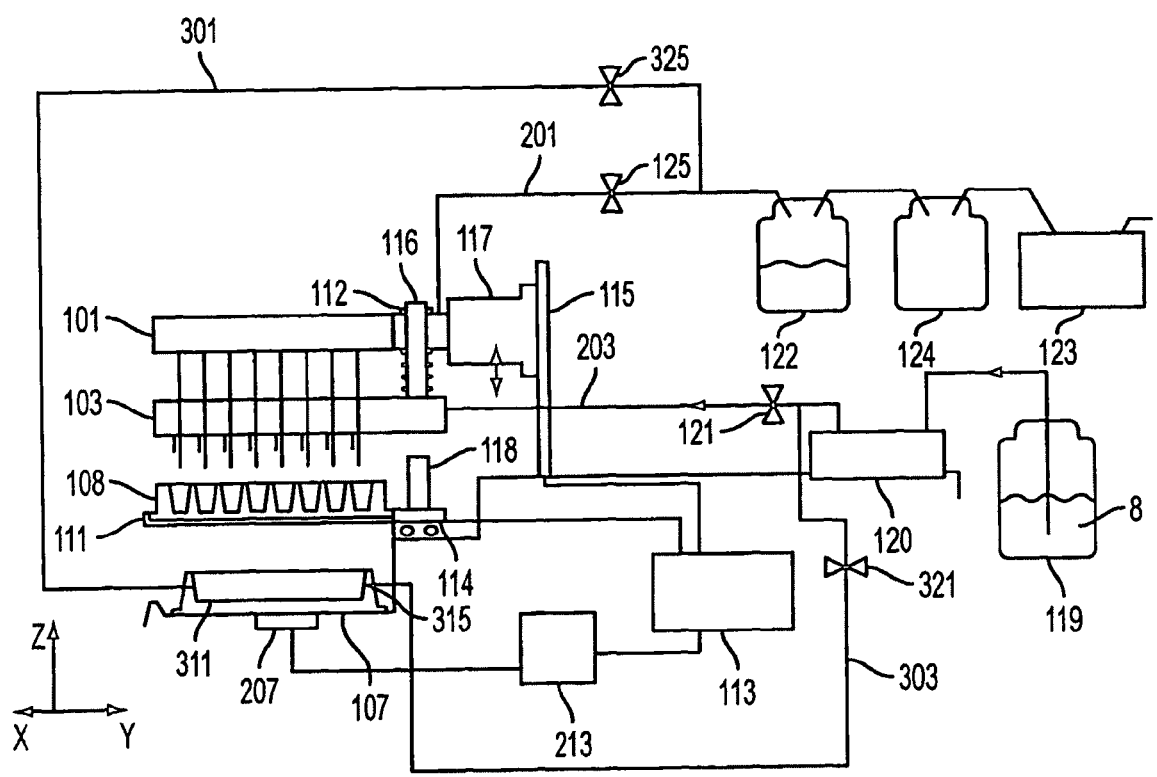
FIG. 5 is a schematic of a third embodiment of the well plate washing system having tank fill and aspirate ports.

Further, according to a third non-limiting embodiment shown in FIG. 5, the fluids used for cleaning of the tubes (e.g., detergent and DiH2O) can be introduced to and evacuated from the tank 107 through ports 313, 311. Dispense and aspirate lines 303, 301, with valves 321, 325, provide the appropriate fluid from the source container (e.g., 119 or one of 119A-D). Again, the controllers 113, 213 can control the dispensation and evacuation of fluid.

According to another non-limiting embodiment of the invention, the relative depths of fluid within the wells 4 of the microplate 3 are sensed in order to monitor whether the dispense or aspirate operations are functioning properly. The sensing of proper functioning of the dispense or aspirate operations can be applied manually at the operator's discretion, can be conducted automatically at regularly scheduled intervals, or can be part of a maintenance operation in which the plate washer automatically performs a cleaning operation of the aspirate and/or dispensing pipes 102, 104 upon determining that the function is impaired until the desired performance is achieved. Non-limiting examples of liquid level sense technology that can be used to determine volumetric performance issues on board the micro plate washing system are capacitive, ultrasonic, optical, and direct contact measurements.

The volumetric function of a well plate washer may include dispensing, aspirating, or a simultaneous combination of both dispensing and aspirating to achieve a user-requested volume of fluid within one or more wells of a plate with a specified accuracy and precision. Accuracy is a measure of the total volume of fluid in the wells, and can be generally expressed as a percent difference from the expected volume averaged over a specified number of wells. The accuracy may be measured gravimetrically, optically, sonically, or by other mechanical means (e.g. other types of level sensing technology). Precision is a measure of the distribution of fluid in the wells of the plate, and is generally expressed by the percent coefficient of variation, which is computed as the standard deviation of a specified set of wells divided by the arithmetic mean of the same wells. The precision is typically measured using optical, ultrasonic, or other mechanical means. Parameters that may alter the volumetric function of the device, such as the chemical composition of the test fluid, the flow rate, the dispense height (z), and the horizontal dispense positions (x and y), are typically stated to describe the conditions under which the accuracy and precision are defined.

In one non-limiting example of measuring the dispense accuracy gravimetrically, the user places a clean dry plate on a scale and measures the Tare weight of the empty plate. The user then places the plate on the carrier of the dispenser, or washer, and a specified volume of fluid is dispensed to the wells of the plate. After the fluid has been dispensed to the plate, the plate is placed on the scale. The volume of fluid dispensed to the wells of the plate may then be computed by dividing the weight of the fluid in the plate by the density of the fluid. Gravimetric measurements are suitable for quantifying dispense accuracy. However, because the measurement is integrated over the entire plate, gravimetric methods are not capable of assessing dispense precision.

In one non-limiting example of measuring the aspiration accuracy gravimetrically, the user places a clean dry plate on a scale and measures the Tare weight of the plate. User then fills each of the wells with fluid. The plate washer is then used to aspirate a portion, or all, of the fluid from each well of the plate. The plate is then placed on the scale. The volume of fluid remaining in the wells of the plate may then be computed by dividing the weight of the fluid in the plate by the density of the fluid.

In one non-limiting example of measuring the dispense accuracy or precision optically, the user first measures the geometric dimensions of the wells of the plate. The user then instructs the well plate washer, or dispenser, to dispense a test fluid with a known optical density (OD) per unit path length, the distance that the light travels through the fluid, to the wells of the plate. After dispensing the fluid, the user places the plate in an absorbance-capable plate reader that measures the optical density (OD) of the fluid in each well of the plate. To compute the volume of fluid dispensed to each well, the user divides the measured optical density of the fluid in each well by the known optical density per unit path length of the test fluid, and multiplies the calculated path length by the cross-sectional area of the well ($\pi$ times the radius of the well squared).

In one non-limiting example of measuring the aspiration accuracy or precision optically, the user first measures the geometric dimensions of the wells of the plate. The user then fills each well with a test fluid with a known optical density (OD) per unit path length, the distance that the light travels through the fluid. After aspirating the fluid from the plate, the user places the plate in an absorbance-capable plate reader that measures the optical density (OD) of the fluid in each well of the plate. To compute the volume of fluid remaining in each well, the user divides the measured optical density of the fluid in each well by the known optical density per unit path length of the test fluid, and multiplies the calculated path length by the cross-sectional area of the well ($\pi$ times the radius of the well squared).

In one non-limiting example of measuring the dispense or aspiration accuracy or precision using acoustic waves in the ultrasonic frequency range, the user first measures the geometric dimensions of the wells of the plate. The ultrasonic transducer produces an acoustic wave that propagates through the plate and the fluid in the wells of the plate. When the acoustic wave encounters a material boundary, which could be the interface between the plate at the bottom of the well and the fluid in the well or the top of the fluid in the well and the ambient air above the fluid, a portion of the wave is reflected back to the transducer. The electronics of the measurement system record the time shift between the transmitted and reflected signals. The liquid level, or path length, is computed by multiplying the time shift by the speed of sound of the material that the wave is passing through. Once the path length has been calculated, the volume of fluid dispensed or remaining in each well can be computed by multiplying the calculated path length by the cross-sectional area of the well ($\pi$ times the radius of the well squared).

In one non-limiting example of measuring the dispense or aspiration accuracy or precision by using electrical capacitance or electrical resistance, the user first measures the geometric dimensions of the wells of the plate. Both the capacitance and resistance measurements rely on precise motion control of the probe height relative to the plate, and of probes that come in contact the fluid. As the probes touch the fluid, the electrical circuit in the sensor changes, and the change is used to indicate that the surface of the fluid has been reached. The distance from the surface of the carrier to the tip of each of the sensor probes is calibrated, and the user must provide the distance from the surface of the carrier to the bottom of the plate well. The difference between the two distances represents the path length, and the volume of fluid dispensed to, or remaining in, the well is computed by multiplying the calculated path length by the cross-sectional area of the well ($\pi$ times the radius of the well squared).

Another possible level sensing technology is based on the change in pressure required to force air through a small orifice that occurs as the exit to the orifice approaches a surface. In one non-limiting example of this technology, a constant stream of air is pushed through an orifice at the end of a probe tip, and a pressure transducer is used to measure the air pressure within the body of the probe. As the probe approaches the surface of the fluid, the pressure within the body of the probe increases. An advantage to this system is that the pressure rise is independent of the fluid in the well, and the magnitude of the rise is sufficiently large that the fluid level (path length) can be determined without contacting the fluid. As with the other level sensing candidates, once the path length is calculated, the calculated path length multiplied by the cross-sectional area of the well ($\pi$ times the radius of the well squared) yields the volume of fluid dispensed to, or remaining in, the wells.

Figure 6A:
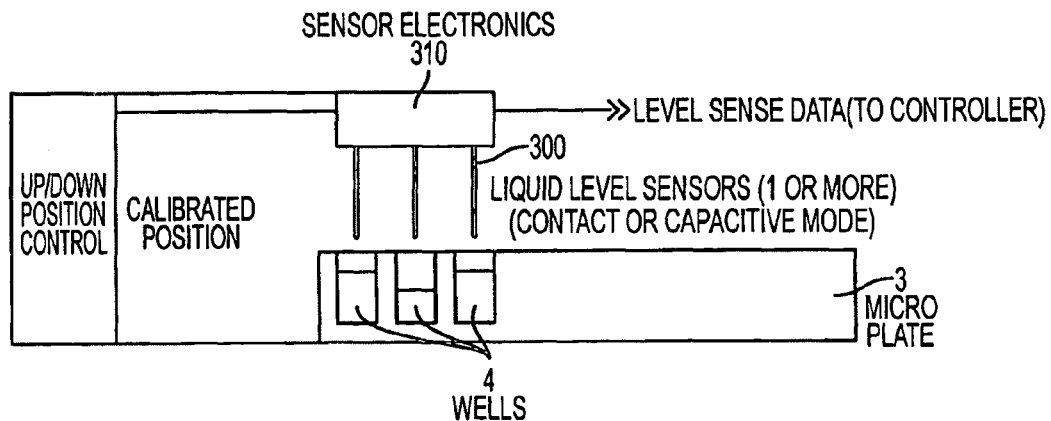
FIGS. 6A and 6B illustrate the use of level sensing technology to determine volumetric or aspirate function of each well.
Figure 6B:
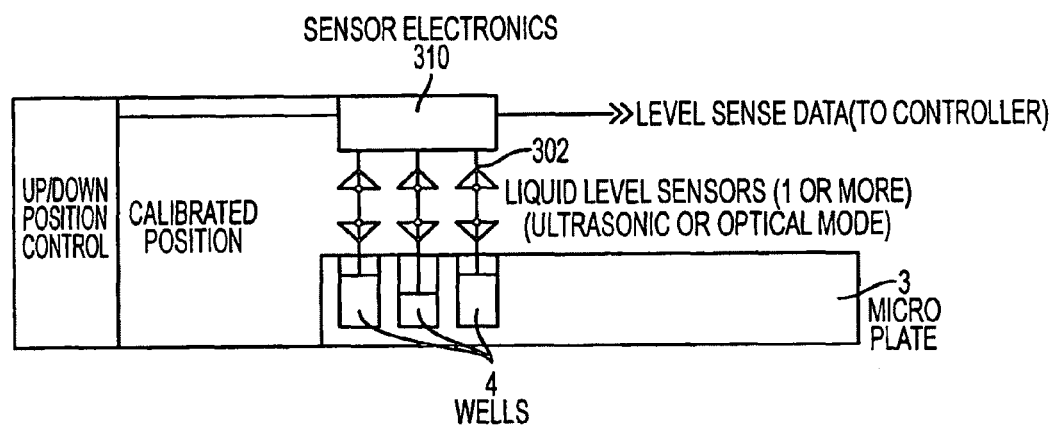

FIGS. 6A and 6B illustrate the use of level sensing system that determines a volumetric function of the wells 4. The level sensing system can include at least one sensing probe 300 or transducer 302 that determines a level of fluid within one or more of the wells 4 and sensor electronics 310 that determine if volumetric function has been impaired based on the sensed level of fluid. By ascertaining the volumetric content of a well 4 using the individual sensing probes 300 or transducers 302, an impaired dispense pipe 102 or aspirate pipe 104 can be detected.

FIG. 6A illustrates a contact or capacitive sensing probe 300. At least one probe 300 is lowered from a calibrated position to a measurement position where the liquid level within the wells 3 is detected. The one or more probes 300 can be moved to detect the level of other wells 4. For example, the one or more probes 300 can be moved so that it is used in adjacent wells 4, allowing the one or more probes 300 to check an entire micro plate matrix. More than one axis of motion is required to accomplish this function. For example, the probes 300 could be in one axis, e.g., moved up and down, and the plate 3 could be moved in the X and Y directions in order to position the one or more probes 300 at the locations for sensing the liquid level in the various wells 4.

FIG. 6B illustrates an optical or ultra sonic sensing transducer 302. Using the optical or ultrasonic transducer 302 is similar to that of the using the probes 300 shown in FIG. 6A. However, the at least one transducer 302 can be lowered from a calibrated position to a measurement position or can remain at a fixed position where the liquid level within the wells 4 is detected.

Sensor electronics 310 can automatically or manually enable cleaning of at least one of the pipes 102, 104 until volumetric function has been restored via repeated processes. Moreover, the sensor electronics 310 can provide a microplate washing process that includes a background task of volumetric verification where a designated zone of said plate is set aside for the purpose of testing volumetric function, or the sensor electronics can provide volumetric function as a maintenance operation aside from normal operations.

Figure 7:
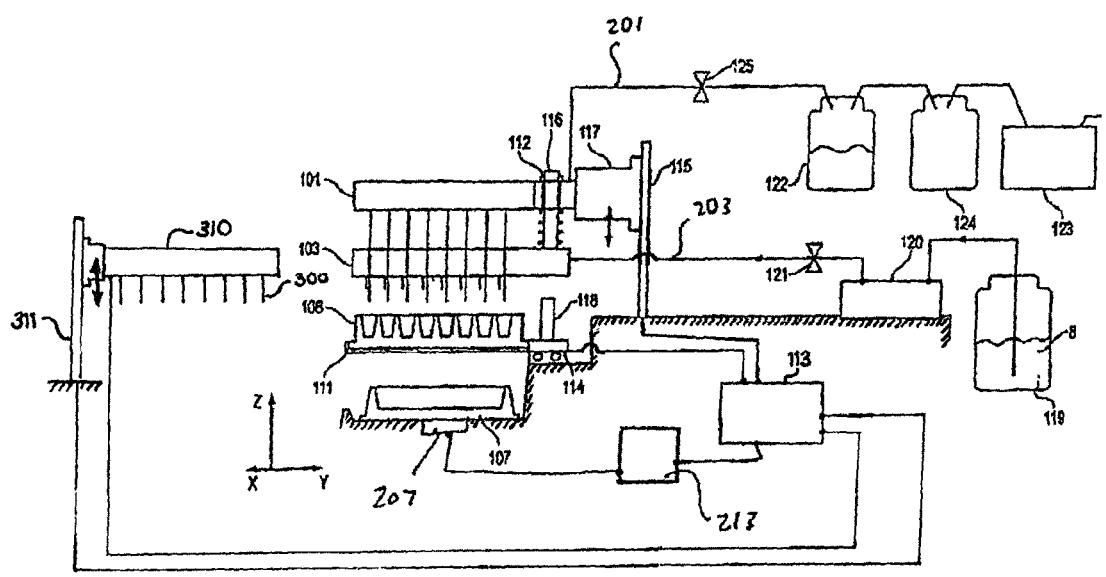
FIG. 7 is a schematic of a third embodiment of the well plate washing system having an integrated level sensing technology to determine a volumetric or aspirate function of each well.

FIG. 7 illustrates an exemplary embodiment of the plate washing system including multiple level sensing probes 300 and associated level sensing electronics 310. The level sensing system 300, 310 is mounted to a linear guide 311 and the vertical position of the level sensing system 300, 310 is controlled by the system controller 113. To sense the level within the plate 108, the system controller 113 shifts the well plate 108 and the plate carrier 111 in the X-Y plane to align the wells with the level sensing probes 300. As the level sensing probes 300 are positioned vertically within each well of the plate 108, the level sense data is sent to the plate washing system controller 113. The system controller 113 analyzes the level sense data to determine if the volumetric function of one or more of the pipes 102, 104 has been impaired.

When the volumetric function of the pipes 102, 104 has been impaired sufficiently, the system controller 113 moves the well plate 108 and carrier 111 out from beneath the pipes 102, 104 so that the pipes 102, 104 may be lowered into the tank 107 for cleaning.

Figure 8:
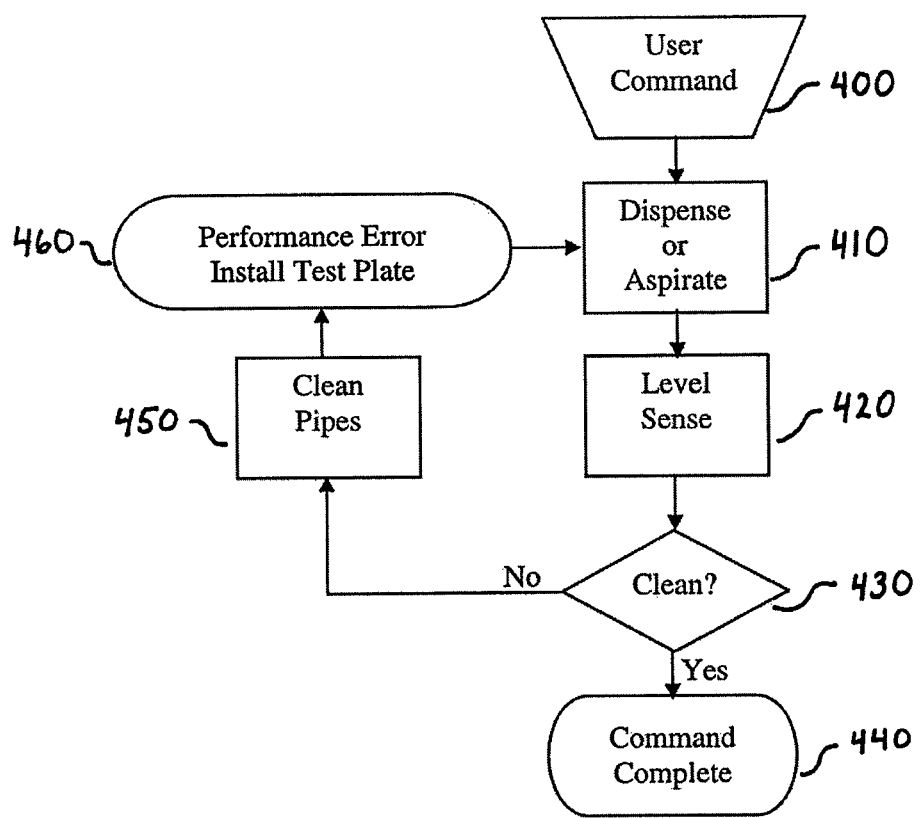
FIG. 8 is a flow chart indicating the operations involved in an automated method of cleaning the pipes of a plate washing system.

FIG. 8 is a flow chart showing an example of the operations involved in an automated method of cleaning the pipes of a plate washing system. In operation 400, a user inputs a series of dispense or aspiration parameters, including the flow rate, volume, dispense height (distance from the surface of the carrier in the z direction), and horizontal dispense position (distance in the x and y directions from the center of the well). The plate washing system then performs the dispense or aspiration through the pipes in operation 410. Before returning the plate to its home position, the plate washing system measures the fluid levels in the wells by performing a level sensing operation in operation 420. Based on the results of the level sensing operation 420, the plate washing system determines whether the pipes are clean in operation 430. If the pipes are determined to be clean in operation 430, then no cleaning is required, and the method is complete (operation 440). However, if the pipes are determined not to be clean in operation 430, then the pipes are cleaned in operation 450, and the system prompts the user to remove the current plate and to install a test plate to allow the user to re-run the method in operation 460, starting with operation 410.

Within the level sensing operation 420, a number of operations may be performed as described above. First, the plate is positioned beneath or above the liquid level sensing transducers, such that the first well to be measured is aligned with the level sensing system. In the case of an optical level sensing system, there is a transmitter below the plate and a detector above the plate.

Second, the path length is calculated as described above. For the capacitance, resistance, and air pressure level sensing technologies, the level sensing probes are lowered, the position of the probe is recorded when the surface of the fluid is detected, the path length is computed, and the probe is raised to a plate clearance height. For the optical and ultrasonic level sensing technologies, the sensor is activated, the time shift in the acoustic waves or the optical density is measured, and the path length is computed.

Third, the plate is repositioned to align the plate for measuring the liquid level of the next well. The above operations are repeated until the liquid level of every well has been measured. The coefficient of variation is then computed by using the path length data, and the coefficient of variation is compared with the performance specifications of the product or some other measure of performance, such as historical data for a particular instrument.

It is of course understood that departures can be made from the preferred embodiment of the invention by those of ordinary skill in the art without departing from the spirit and scope of the invention that is limited only by the following claims and their legal equivalents. For example, the invention is not limited to the specific structures and processes discussed above.

What is claimed is:

1. A plate washing system, comprising:
   at least one manifold having a plurality of pipes configured to be provided within wells of a plate in order to wash the wells when the plate is in a washing position, wherein the plurality of pipes includes a plurality of dispense pipes;
   a tank that is capable of being filled with a fluid;
   an ultrasonic transducer mounted to the tank;
   a liquid level sensor including at least one probe; and
   a control system configured:
      to move the plate between the washing position and a sensing position, wherein the liquid lever sensor is aligned with the plate;
      to relatively move the at least one probe and the plate to sense a liquid level in one or more wells to determine, based on the sensed liquid level, whether a volumetric function of the dispense pipes has been impaired;
      to position the plurality of pipes within the tank; and
      to activate the ultrasonic transducer in order to vibrate the fluid within the tank when tips of the plurality of pipes are positioned within the tank and when the volumetric function of the dispense pipes has been impaired.

2. The system of claim 1, wherein the control system controls movement of at least one of the manifold and the tank in order to position the tips of the pipes within the tank.

3. The system of claim 1, wherein the control system automatically controls movement of at least one of the at least one manifold and the tank so that the plurality of pipes are positioned within the tank, and automatically activates the ultrasonic transducer in order to vibrate the fluid within the tank.

4. The system of claim 3, wherein said plate is a microtiter plate.

5. The system of claim 1, wherein said plurality of pipes includes a plurality of dispense pipes, wherein said control system controls the dispense pipes so that the dispense pipes dispense the fluid within the tank.

6. The system of claim 5, wherein the plurality of pipes further include a plurality of aspirate pipes, wherein the control system controls the aspirate pipes so that the aspirate pipes evacuate the fluid from the tank.

7. The system of claim 1, wherein the control system is programmed to automatically control at least one of fluid changes, soak times, and cleaning times.

8. The system of claim 6, wherein the control system is programmed to control at least one of fluid changes, soak times, and cleaning times.

9. The washing system of claim 1, wherein when the ultrasonic transducer is activated, a voltage of a predetermined amplitude and frequency is applied to the ultrasonic transducer.

10. The system of claim 9, wherein the applied voltage is 30-300 Volts and has a frequency of 40-100 kHz.

11. The system of claim 6, wherein the control system is programmed to control filling and evacuation of the tank.

12. The system of claim 1, wherein the control system is programmed to automatically control filling and evacuation of the tank.

13. The system of claim 12, wherein said tank includes a fill port and an aspirate port, said fluid being introduced into the tank through the fill port and said fluid being evacuated from the tank through the aspirate port.

14. A method of cleaning pipes of a plate washing system, comprising:
   providing the plate washing system, wherein the plate washing system comprises:
      at least one manifold having a plurality of pipes configured to be provided within wells of a plate in order to wash the wells, when the plate is in a washing position, wherein the plurality of pipes includes a plurality of dispense pipes;
      a tank that is capable of being filled with a fluid; an ultrasonic transducer mounted to the tank; and a control system;

filling the tank with a fluid;
moving the plate from washing to sensing position, wherein the plate is aligned with a sensor, comprising at least one probe;
relatively moving the at least one probe and the plate to sense a liquid level in one or more wells to determine, based on the sensed liquid level, whether a volumetric function of the dispense pipes has been impaired;
positioning the plurality of pipes within the tank, and
activating the ultrasonic transducer in order to vibrate the fluid within the tank when tips of the plurality of pipes are positioned within the tank and when the volumetric function of the dispense pipes has been impaired.

15. The method of claim 14, wherein the control system controls movement of the at least one of the manifold and the tank in order to position the tips of the pipes within the tank.

16. The method of claim 14, wherein the control system automatically controls movement of at least one of the at least one manifold and the tank so that the plurality of pipes are positioned within the tank, and automatically activates the ultrasonic transducer in order to vibrate the fluid within the tank.

17. The method of claim 16, wherein said plate is a microtiter plate.

18. The method of claim 14, wherein said plurality of pipes includes a plurality of dispense pipes, wherein said control system controls the dispense pipes so that the dispense pipes dispense the fluid within the tank.

19. The method of claim 18, wherein the plurality of pipes further include a plurality of aspirate pipes, wherein the control system controls the aspirate pipes so that the aspirate pipes evacuate the fluid from the tank.

20. The method of claim 14, wherein the control system is programmed to automatically control at least one of fluid changes, soak times, and cleaning times.

21. The method of claim 19, wherein the control system is programmed to control at least one of fluid changes, soak times, and cleaning times.

22. The method of claim 14, wherein when the ultrasonic transducer is activated, a voltage of a predetermined amplitude and frequency is applied to the ultrasonic transducer.

23. The method of claim 22, wherein the applied voltage is 30-300 Volts AC with a frequency of 50-60 kHz.

24. The method of claim 19, wherein the control system is programmed to control filling and evacuation of the tank.

25. The method of claim 14, wherein the control system is programmed to automatically control filling and evacuation of the tank.

26. The method of claim 25, wherein said tank includes a fill port and an aspirate port, said fluid being introduced into the tank through the fill port and said fluid being evacuated from the tank through the aspirate port.

27. The system of claim 1, further comprising a level sensing system, said level sensing system comprising:
at least one sensing probe or transducer that senses a level of fluid within one or more of said wells of the plate; and
sensor electronics that determine if a volumetric function of the pipes has been impaired based on the sensed level of fluid.

28. The system of claim 27, wherein said sensor electronics automatically enable cleaning of at least one of said plurality of pipes until the volumetric function of the pipes has been restored via repeated processes.

29. The system of claim 27, wherein said sensor electronics manually enable cleaning of at least one of said plurality of pipes until the volumetric function of the pipes has been restored via repeated processes.

30. The system of claim 27, wherein said sensor electronics provide a plate washing process that includes a background task of volumetric verification where a designated zone of said plate is set aside for the purpose of testing the volumetric function of the pipes.

31. The system of claim 27, wherein said sensor electronics provide the volumetric function of the pipes as a maintenance operation aside from normal operations.

32. The method of claim 14, further comprising:
sensing a level of fluid within one or more of said wells of the plate using at least one sensing probe or transducer; and
determining if a volumetric function has been impaired based on the sensed level of fluid.

33. The method of claim 32, further comprising automatically enabling cleaning of at least one of said plurality of pipes until the volumetric function of the pipes has been restored via repeated processes.

34. The method of claim 32, further comprising manually enabling cleaning of at least one of said plurality of pipes until the volumetric function of the pipes has been restored via repeated processes.

35. The method of claim 32, wherein determining a volumetric function is a background task of volumetric verification where a designated zone of said plate is set aside for the purpose of testing the volumetric function of the pipes.

36. The method of claim 32, wherein determining the volumetric function of the pipes is a maintenance operation aside from normal operations.

37. An automated method of cleaning pipes of a plate washing system, the method comprising:
dispensing a volume of fluid through the pipes and into wells of a plate;
sensing a level of fluid within at least one well of the plate using a liquid level sensor including a probe;
moving the plate between the washing position and a sensing position, wherein the liquid level sensor is aligned with the plate;
relatively moving the probe and the plate to sense a liquid level in one or more wells to determine, based on the sensed liquid level, whether a volumetric function of the dispense pipes has been impaired, wherein the volumetric function comprises dispensing the volume of fluid with a specified precision;
positioning the plurality of pipes within a tank, and
automatically activating an ultrasonic transducer in order to vibrate the fluid within the tank when tips of the plurality of pipes are positioned within the tank and when the volumetric function of the dispense pipes has been impaired.

38. An automated method of cleaning pipes of a plate washing system, the method comprising:
dispensing a volume of fluid through the pipes and into wells of a plate;
sensing a level of fluid within at least one well of the plate using a liquid level sensor including a probe; moving the plate between the washing position and a sensing position, wherein the liquid level sensor is aligned with the plate; and
relatively moving the at least one probe and the plate to sense a liquid level in one or more wells to determine, based on the sensed liquid level, whether a volumetric function of the dispense pipes has been impaired, wherein the volumetric function comprises dispensing the volume of fluid with a specified accuracy;

positioning the plurality of pipes within a tank; and automatically activating an ultrasonic transducer in order to vibrate the fluid within the tank when tips of the plurality of pipes are positioned within the tank and when the volumetric function of the dispense pipes has been impaired.

39. The automated method of claim 38, wherein the volumetric function further comprises dispensing the volume of fluid with a specified precision.

40. The automated method of claim 37, further comprising repeating the dispensing, sensing, determining, and automatically cleaning operations until the volumetric function has been restored.

41. The automated method of claim 38, further comprising repeating the dispensing, sensing, determining, and automatically cleaning operations until the volumetric function has been restored.

42. The automated method of claim 37, wherein the sensing comprises:

aligning a well of the plate to be measured with a level sensing system;

using the level sensing system to calculate a path length of the fluid within the well;

adding the calculated path length to a path length data file; and repeating the aligning, calculating, and adding operations for each well of the plate to be measured.

43. The automated method of claim 42, wherein the determining comprises:

calculating a coefficient of variation of the volume dispensed in the wells based on the path length data in the path length file; and comparing the coefficient of variation with a predetermined indicator.

44. The automated method of claim 38, wherein the sensing comprises:

aligning a well of the plate to be measured with a level sensing system;

using the level sensing system to calculate a path length of the fluid within the well;

adding the calculated path length to a path length data file; and repeating the aligning, calculating, and adding operations for each well of the plate to be measured.

45. The automated method of claim 44, wherein the determining comprises:

calculating a volume dispensed in each well by multiplying the path length of each well by the cross-sectional area of each well;

calculating a total volume dispensed in the plate by adding the volume dispensed in each well; and comparing the total volume with a predetermined indicator.

46. The automated method of claim 42, wherein the using the level sensing system to calculate a path length of the fluid within the well comprises:

using a plate reader to measure an optical density of the fluid in the well; and calculating a path length of the fluid in the well by dividing the measured optical density by a known optical density per unit path length.

47. The automated method of claim 42, wherein the using the level sensing system to calculate a path length of the fluid within the well comprises:

using the ultrasonic transducer to produce an acoustic wave that propagates through the plate and the fluid in the well;

measuring a time shift between a portion of the acoustic wave that is transmitted through the fluid in the well and a portion of the acoustic wave that is reflected from the fluid in the well; and calculating a path length of the fluid in the well by multiplying the time shift by the speed of sound of the fluid in the well.

48. The automated method of claim 42, wherein the using the level sensing system to calculate a path length of the fluid within the well comprises:

using a probe to sense the top of the fluid in the well by detecting a change in electrical capacitance or electrical resistance; and calculating a path length of the fluid based on the difference between a distance between the top of the fluid and the bottom of the well.

49. The automated method of claim 42, wherein the using the level sensing system to calculate a path length of the fluid within the well comprises:

pushing a constant stream of air through an orifice at an end of a probe tip;

using a pressure transducer to measure an air pressure within a body of a probe as the probe moves through the fluid in the well; and calculating a path length of the fluid in the well based on the pressure measurements.

50. An automated method of cleaning pipes of a plate washing system, the method comprising:

aspirating a volume of fluid from wells of a plate through the pipes when the plate is in a washing position, wherein the plurality of pipes includes a plurality of aspirate pipes;

sensing a level of fluid within at least one well of the plate using a liquid level sensor including at least one probe;

moving the plate between the washing position and a sensing position, wherein the liquid lever sensor is aligned with the plate;

relatively moving the at least one probe and the plate to sense a liquid level in one or more wells to determine, based on the sensed liquid level, whether a volumetric function of the aspirate pipes has been impaired; wherein the volumetric function comprises aspirating the volume of fluid with a specified precision;

positioning the plurality of pipes within a tank; and automatically activating an ultrasonic transducer in order to vibrate the fluid within the tank when tips of the plurality of pipes are positioned within the tank and when the volumetric function of the aspirate pipes has been impaired to clean the pipes.

51. An automated method of cleaning pipes of a plate washing system, the method comprising:

aspirating a volume of fluid from wells of a plate through the pipes when the plate is in a washing position, wherein the plurality of pipes includes a plurality of aspirate pipes;

sensing a level of fluid within at least one well of the plate using a liquid level sensor including a probe;

moving the plate between the washing position and a sensing position, wherein the liquid lever sensor is aligned with the plate;

relatively moving the at least one probe and the plate to sense a liquid level in one or more wells to determine, based on the sensed liquid level, whether a volumetric function of the aspirate pipes has been impaired; wherein the volumetric fluid comprises aspirating the volume of fluid with a specified accuracy;

positioning the plurality of pipes within a tank; and activating an ultrasonic transducer in order to automatically vibrate the fluid within the tank when tips of the plurality of pipes are positioned within the tank and when the volumetric function of the aspirate pipes has been impaired to clean the pipes.

52. The automated method of claim 51, wherein the volumetric function further comprises aspirating the volume of fluid with a specified accuracy.

53. The automated method of claim 50, further comprising repeating the aspirating, sensing, determining, and automatically cleaning operations until the volumetric function has been restored.

54. The automated method of claim 51, further comprising repeating the aspirating, sensing, determining, and automatically cleaning operations until the volumetric function has been restored.

55. The automated method of claim 50, wherein the sensing comprises:

aligning a well of the plate to be measured with a level sensing system;

using the level sensing system to calculate a path length of the fluid within the well;

adding the calculated path length to a path length data file; and repeating the aligning, calculating, and adding operations for each well of the plate to be measured.

56. The automated method of claim 55, wherein the determining comprises:

calculating a coefficient of variation of the volume remaining in the wells based on the path length data in the path length file; and comparing the coefficient of variation with a predetermined indicator.

57. The automated method of claim 51, wherein the sensing comprises:

aligning a well of the plate to be measured with a level sensing system;

using the level sensing system to calculate a path length of the fluid within the well;

adding the calculated path length to a path length data file; and repeating the aligning, calculating, and adding operations for each well of the plate to be measured.

58. The automated method of claim 57, wherein the determining comprises:

calculating a volume remaining in each well by multiplying the path length of each well by the cross-sectional area of each well;

calculating a total volume remaining in the plate by adding the volume dispensed in each well; and comparing the total volume with a predetermined indicator.

59. A system with an integrated ultrasonic pipe cleaner for cleaning a plurality of pipes that become dirty from cleaning wells of a plate washing system, the system comprising:

a plate washing system including a plate containing a plurality of wells and at least one manifold;

said at least one manifold having a plurality of pipes configured to be provided within wells of the plate in order to wash the wells when the plate is in a washing position, wherein the plurality of pipes includes a plurality of dispense pipes;

a mechanism for moving the plate away from the plurality of pipes after washing the wells of the plate is completed, wherein, when the plurality of pipes have become dirty from washing the wells of the plate;

a tank that is capable of being filled is filled with a fluid;

a control system for filling the tank with the fluid fills the tank with fluid;

an ultrasonic transducer is mounted to the tank; and a liquid level sensor including a probe; and the control system being configured to move the plate between the washing position and a sensing position, wherein the liquid lever sensor is aligned with the plate;

to relatively move the at least one probe and the plate to sense a liquid level in one or more wells to determine, based on the sensed liquid level, whether a volumetric function of the dispense pipes has been impaired; and to position the plurality of pipes within the tank and to activate the ultrasonic transducer in order to vibrate the fluid within the tank when tips of the plurality of pipes are positioned within the tank and when the volumetric function of the dispense pipes has been impaired, so as to clean the pipes.

60. A plate washing system for washing the wells of a plate, the plate washing system comprising:

a well plate support mechanism having a washing position;

a manifold having a plurality of pipes configured to be provided within wells of a plate in order to wash the wells when the plate is in a washing position, wherein the manifold comprises a dispense manifold and the pipes comprise dispense pipes for providing a wash solution in order to wash the wells;

a support mechanism positioning system for moving the well plate support mechanism into and out of the washing position;

a tank that is capable of being filled with a fluid;

a drive mechanism that moves at least one of the manifold and tank to position the tips of the plurality of pipes within the tank;

an ultrasonic transducer mounted to the tank;

a liquid level sensor including a probe; and a control system, operative when the well plate support mechanism is out of the washing position and is in a sensing position, wherein the liquid lever sensor is aligned with the plate, and to relatively move the at least one probe and the plate to sense a liquid level in one or more wells to determine, based on the sensed liquid level, whether a volumetric function of the dispense pipes has been impaired; and to position the plurality of pipes within the tank that are submerged within the fluid and activate the ultrasonic transducer in order to vibrate the fluid within the tank when tips of the plurality of pipes are positioned within the tank and when the volumetric function of the dispense pipes has been impaired.

61. The plate washing system of claim 60, wherein the control system is operative to control dispensation of the wash solution and a separate cleaning fluid whereby, for cleaning, cleaning fluid is dispensed into the tank and, when tips of said plurality of dispense pipes are submerged in the fluid, to activate the ultrasonic transducer in order to vibrate the fluid within the tank.

* * * * *